(12) United States Patent
Wahlström et al.

(10) Patent No.: US 6,888,045 B2
(45) Date of Patent: May 3, 2005

(54) METHOD OF PRODUCING A FIBROUS MATERIAL LAYER, A FIBROUS MATERIAL LAYER AND AN ABSORBENT ARTICLE CONTAINING SAME

(75) Inventors: Johan Wahlström, Göteborg (SE); Jan Wästlund-Karlsson, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 153 days.

(21) Appl. No.: 10/235,888

(22) Filed: Sep. 6, 2002

(65) Prior Publication Data
US 2003/0093044 A1 May 15, 2003

Related U.S. Application Data
(60) Provisional application No. 60/317,126, filed on Sep. 6, 2001.

(51) Int. Cl.[7] ................................................ A61F 13/15
(52) U.S. Cl. .................... 604/378; 604/384; 604/365; 604/379; 604/380; 604/385.01; 156/166; 156/167; 156/182; 156/196; 156/264; 162/109; 162/111; 162/125
(58) Field of Search ............................... 604/382, 365, 604/384, 383, 378, 379, 380, 385.23, 374, 366, 385; 428/170, 171, 122, 167; 156/166, 167, 182, 196, 250, 264; 162/109, 111, 125, 131; 442/237, 366

(56) References Cited

U.S. PATENT DOCUMENTS

| | | |
|---|---|---|
| 3,371,667 A | 3/1968 | Morse |
| 4,360,022 A | 11/1982 | Usami et al. |
| 4,647,392 A | 3/1987 | Darden et al. |
| 4,798,603 A | 1/1989 | Meyer et al. |
| 5,382,245 A | 1/1995 | Thompson et al. |
| 5,669,895 A | 9/1997 | Murakami et al. |
| 6,093,474 A | 7/2000 | Sironi |

FOREIGN PATENT DOCUMENTS

| | | |
|---|---|---|
| EP | 312 118 | 4/1989 |
| EP | 391 814 | 10/1990 |
| EP | 937 792 | 8/1999 |
| GB | 2 209 672 | 5/1989 |
| WO | WO 90/14814 | 12/1990 |
| WO | 99/27876 | 6/1999 |
| WO | 99/30661 | 6/1999 |

Primary Examiner—Jacqueline F. Stephens
(74) Attorney, Agent, or Firm—Young & Thompson

(57) ABSTRACT

A fibrous material and a method of producing it, the material is mainly intended to be incorporated in an absorbent article and comprises a layer of continuous fibers, so-called tow, which have been bonded together in points, lines or spots in a bonding pattern, but otherwise are substantially unbonded to each other. The tow layer is bonded with at least two bonding patterns: a first relatively strong and diffuse bonding pattern, and a second more distinct second bonding pattern. Bonding of at least the first bonding pattern takes place by thermobonding, wherein a pattern roll is used which provide the desired bonding patterns. In the first welding step the pattern roll is driven at a higher speed than the feeding speed of the tow layer, so as to create a relatively diffuse and strong bonding pattern.

21 Claims, 3 Drawing Sheets

METHOD OF PRODUCING A FIBROUS MATERIAL LAYER, A FIBROUS MATERIAL LAYER AND AN ABSORBENT ARTICLE CONTAINING SAME

This application claims benefit of U.S. Provisional 60/317,126 filed Sep. 6, 2001.

TECHNICAL FIELD

The present invention relates to a method of producing a fibrous material layer mainly intended for being incorporated in an absorbent article, such as a diaper, pant diaper, incontinence guard, sanitary napkin, wound dressing and the like. It further refers to a fibrous material layer and an absorbent article containing same.

BACKGROUND OF THE INVENTION

Absorbent articles of the above-mentioned kind are intended for absorption of body fluids, such as urine and blood. As a liquid pervious topsheet, facing the wearer during use, they usually exhibit a nonwoven material, for example of spunbond-type. It is also previously known to arrange a liquid acquisition layer between the top layer and the absorbent body, said liquid acquisition layer having the ability to quickly receive large quantities of liquid, and to distribute the liquid and temporarily store it before it is absorbed by the underlying absorbent body. This is of great importance, especially in the thin compressed absorbent bodies of today, often comprising a high content of so called superabsorbents, which certainly have a high absorption capacity but in many cases a too low absorption rate in order to momentously be able to absorb the large quantity of liquid which can be discharged within a few seconds during urination. A porous, relatively thick acquisition layer, for example in the form of a fibrous wadding, a carded fibrous web, or another type of fibrous material, has a high instantaneous liquid-receiving capacity and is able to store the liquid temporarily until it has been absorbed by the absorbent body. The same applies for porous foam materials. The liquid is thereafter drained successively into the adjacent absorbent body, after which the acquisition layer once again has the capacity to receive liquid from a repeated wetting.

Examples of absorbent articles comprising such porous acquisition layers are, for example, disclosed in U.S. Pat. No. 3,371,667, EP-A-0,312,118 and EP-A-0,474,777.

The materials used today as acquisition layers in absorbent articles are mostly functioning well, but are relatively expensive and can sometimes exhibit an insufficient acquisition rate, especially in the second and third wettings, if large quantities of liquid are involved. Furthermore, they are difficult to process and store due to their bulkiness.

It is previously known through EP-A-0,391,814 and GB-B2,209,672 to use continuous, unbonded synthetic fibres, so-called tow, in absorbent articles for distributing liquid in the longitudinal direction of the article.

It is further known through WO 99/27876 to provide a tow layer used in an absorbent article as an acquisition and/or topsheet material and which has been bonded in points, lines or spots in a bonding pattern, but where the tow filaments otherwise are substantially unbonded to each other. This material layer exhibits a high acquisition rate for liquid also when repeatedly wetted, exhibits a high strength in longitudinal direction, high resistance and high comfort. One problem that may occur with this type of material is that it is difficult to achieve a high strength in the transverse direction, since said strength being provided solely by the bonding pattern.

OBJECT AND MOST IMPORTANT FEATURES OF THE INVENTION

The object of the present invention is to provide a method of producing a tow layer of the above kind, which exhibits an improved strength especially in the transverse direction. According to the invention, this has been achieved by the fact that bonding is performed in two steps: a first step wherein bonding takes place by thermobonding, such as ultrasonic welding or laser welding, at which a pattern roll is used which provides the desired bonding pattern, said pattern roll being driven at a higher speed than the feeding speed of the tow layer, so as to create a relatively diffuse and strong bonding pattern in the tow layer; and a second step in which a more distinct second bonding pattern is created.

Preferably that said first and second bonding patterns are applied so as to overlap with each other over at least a substantial part of the bonded area of said fibrous material layer. A substantial portion in this respect means at least 50% of the bonded area of the fibrous layer.

It is further preferred that that also in the second step bonding takes place by thermobonding, such as ultrasonic welding or laser welding, at which a pattern roll is used which provides the desired bonding pattern, wherein in the second bonding step the pattern roll is driven at substantially the same speed as the feeding speed of the tow layer.

In a preferred embodiment the tow layer is in the second step laminated to a web of material, such as a nonwoven layer, with said second bonding pattern.

The invention further refers to a fibrous material layer mainly intended for being incorporated in an absorbent article, said material layer comprises a layer of continuous fibres, so-called tow, which have been bonded together in points, lines or spots in a bonding pattern, but otherwise are substantially unbonded to each other, wherein the tow layer is bonded with at least two bonding patterns:

a first relatively strong and diffuse bonding pattern provided by thermobonding, and a second more distinct bonding pattern;

said first and second bonding patterns are arranged so as to overlap with each other over at least a substantial part of the bonded area of said fibrous layer.

The invention also refers to an absorbent article such as a diaper, pant diaper, incontinence guard, sanitary napkin, wound dressing and the like, of the kind comprising a liquid permeable topsheet, a liquid impervious backsheet and an absorbent body arranged therebetween, wherein the article comprises a tow layer of the kind stated above.

The layer can be used as a liquid acquisition layer underneath a topsheet, as a topsheet, or as an integrated topsheet/liquid acquisition layer.

Further features of the invention are evident from the following description and the claims.

DESCRIPTION OF THE DRAWINGS

The invention will below be closer described with reference to some of the embodiments shown in the accompanying drawings.

DESCRIPTION OF EMBODIMENTS

Figure 1:
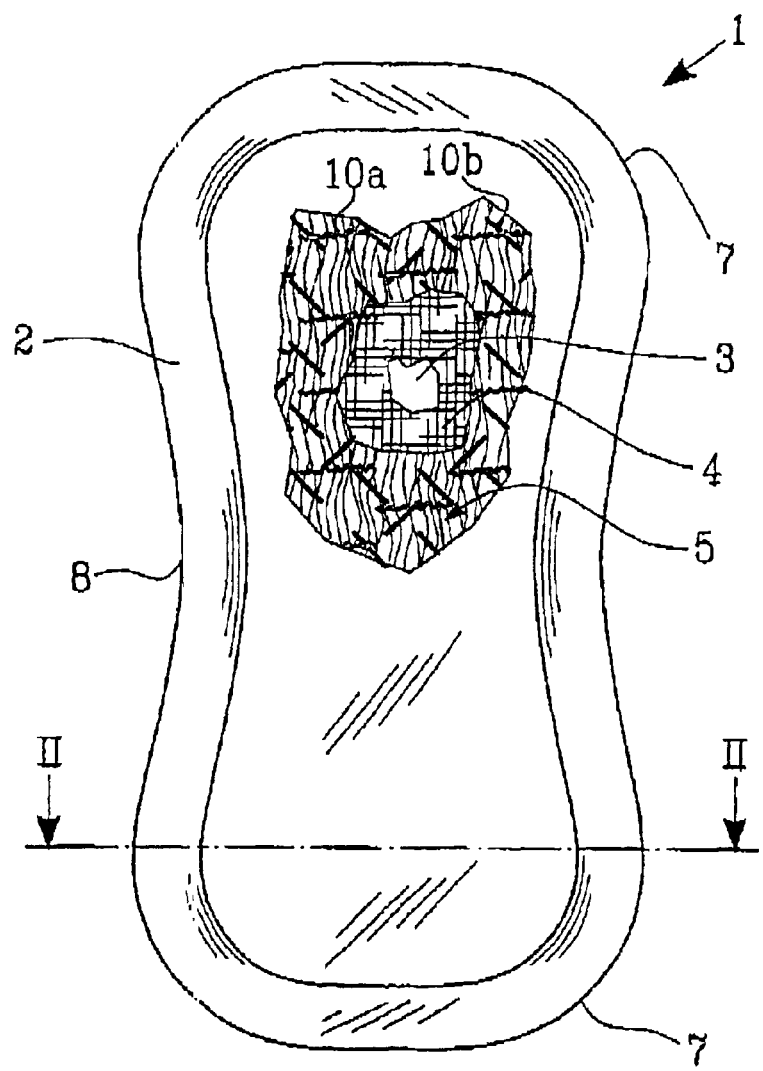
FIG. 1 is a plan view of an absorbent article in the form of an incontinence guard.
Figure 2:
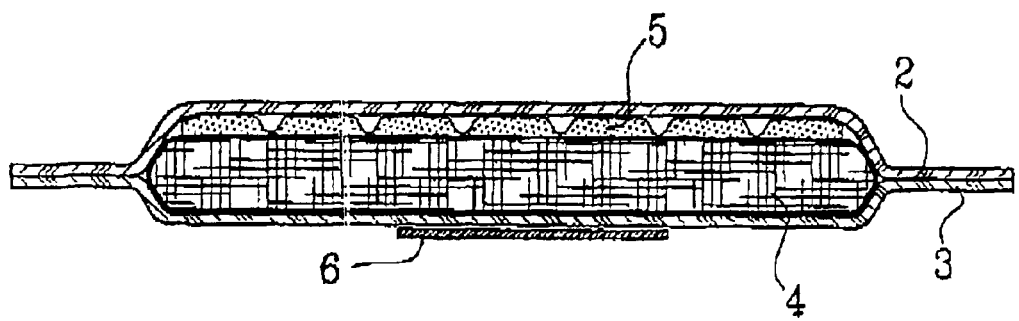
FIG. 2 is a section according to the line II—II in FIG. 1.

FIGS. 1 and 2 show schematically an example of an incontinence guard 1 comprising a liquid pervious topsheet 2, a liquid impervious backsheet 3 and a absorbent body 4 enclosed therebetween. A porous resilient liquid acquisition layer 5 is arranged between the liquid pervious topsheet 2 and the absorbent body 4.

The liquid pervious topsheet 2 can comprise a nonwoven material, for example a spunbond material of synthetic filaments, a meltblown material, a thermobonded material or a bonded carded fibrous material. The liquid impervious backsheet 3 can consist of a plastic film, a nonwoven material which is coated with a liquid impervious material or a hydrophobic nonwoven material which resists liquid penetration.

The topsheet 2 and the backsheet 3 have a larger surface area than the absorbent body 4 and the liquid acquisition layer 3 and extend outside the edges thereof. The layers 2 and 3 are interconnected within the projecting portions, for example by gluing or welding with heat or ultrasonic.

The absorbent body 4 can be of any conventional kind. Examples of common absorption materials are cellulosic fluff pulp, tissue layers, highly absorbent polymers (so called superabsorbents), absorbent foam materials, absorbent nonwoven materials and the like. It is common to combine cellulosic fluff pulp with superabsorbents in an absorbent body. It is also common to have absorbent bodies comprising layers of different materials with different properties concerning liquid acquisition capacity, liquid distribution capacity and liquid storage capacity. This is wellknown for the person skilled in the art and need not be described in detail. The thin absorbent bodies which are common in for example baby diapers and incontinence guards often consist of a compressed mixed or layered structure of cellulosic fluff pulp and superabsorbent.

On the outside of the liquid impervious backsheet 3 fastening means in the form of strips 6 of a self adhesive glue are arranged. An incontinence guard of the kind shown in FIG. 1 is mainly intended to be used by persons suffering from a relatively light incontinence and is easily worn in ordinary underpants. The fastening means 6 serve to keep the incontinence guard in place in the underpants during use. A number of other types of glue patterns, for example transverse, are of course possible as well as other types of fastening means such as hook and loop, snap fasteners, girdles, special under-pants or the like.

The incontinence guard is hour glass shaped with broader end portions 7 and a more narrow crotch portion 8 located between the end portions. The crotch portion 8 is the portion of the incontinence guard that is intended during use to be worn in the crotch between the legs of the wearer and serve as a receiving portion for the discharged body fluid.

It should be noted that the incontinence guard shown in the drawings and described above only is a non-limiting example of an absorbent article. Thus the shape of the article as well as the construction thereof can be varied. The absorbent article can also be a diaper, a pant diaper, a sanitary napkin or the like. The absorbent article can be disposable or reuseable. For reuseable articles other materials than the above described are however used as a liquid pervious topsheet and absorbent body respectively.

Between the liquid pervious topsheet 2 and the absorbent body 4 there is arranged a porous and resilient acquisition layer 5 having the ability to quickly receive large amounts of liquid and distribute the liquid and store it temporarily before it is absorbed by the underlying absorbent body 4. This ability should be essentially maintained also after wetting of the material. The acquisition layer 5 can either cover the entire absorbent body 4, extend outside thereof or cover only part of the central portions of the absorbent body.

Figure 3:
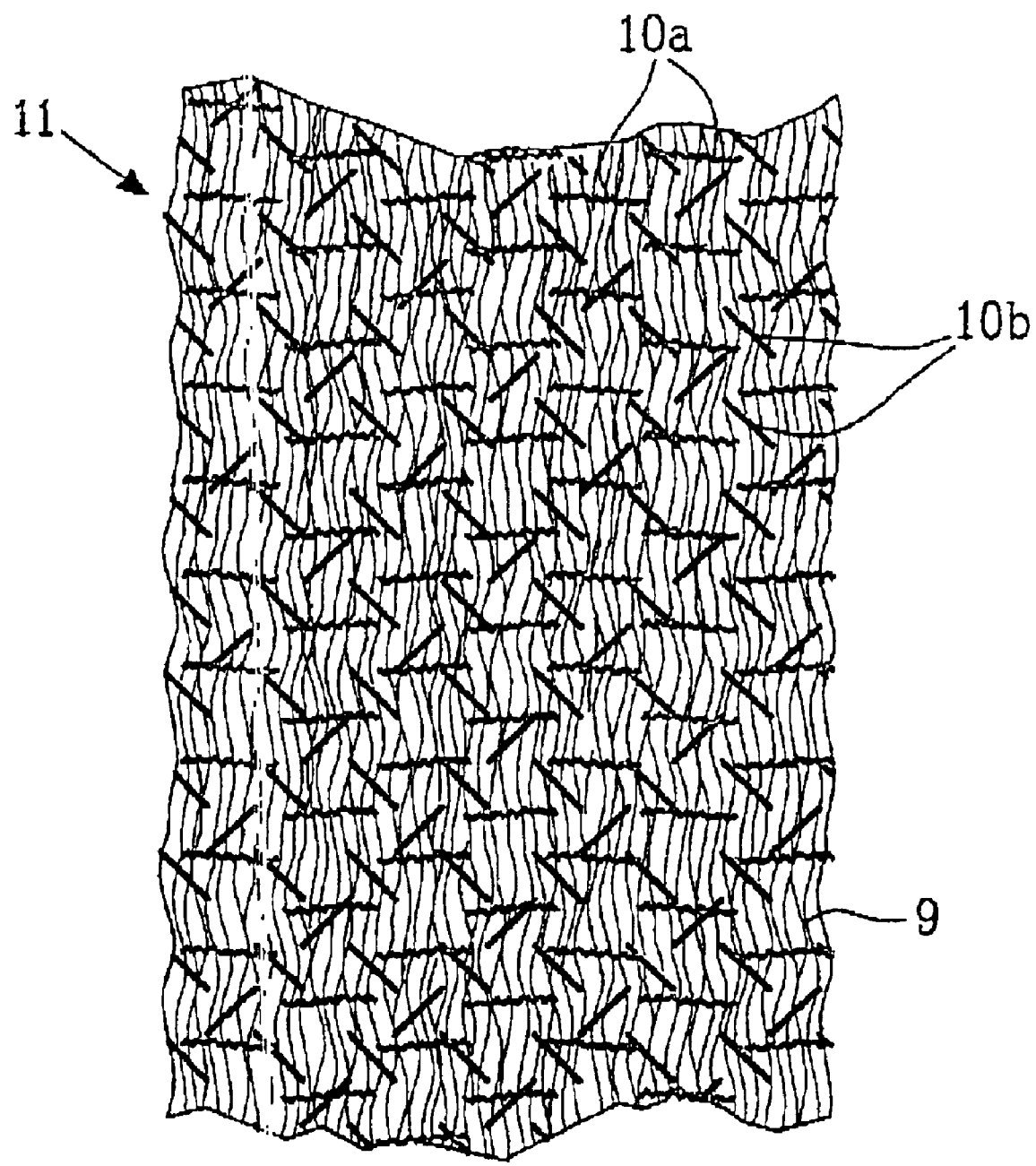
FIG. 3 shows schematically a piece of a fibrous material layer according to the invention.

According to the invention the acquisition layer 5 consists of a layer of continuous filaments or fibers 9, so called tow fibers, which have been bonded together in points, spots or lines forming a bonding pattern 10, but otherwise are substantially unbonded to each other. In the embodiment shown in FIGS. 1 and 3 the bonding pattern 10 is a pattern of lines with short lines arranged in a zigzag configuration. The bonding pattern is achieved by for example ultra sonic welding or other thermal bonding. Examples of other suitable thermal bonding methods are pattern calendering, laser bonding etc. This implies that at least some of the fibers in the tow are thermoplastic. Examples of thermo-plastic fibers are polyolefines, polyamides, polyester and the like. Also so called bicomponent fibers are included. The choice of bonding type is mainly decided by which type of fibers are used in the tow.

The design of the bonding pattern 10 can of course vary within wide limits. The pattern may be in the form of points, spots or preferably lines. The lines may be straight as well as curved and the length can vary from a few millimeters to extending transversely or diagonally across the entire article. Preferably the lines extend across or obliquely across the longitudinal direction of the tow fibers 9, so that a plurality of tow fibers are bonded to each other by each bonding line. It is also an advantage if different bonding lines overlap each other as seen across the longitudinal direction of the tow fibers, so that a main part of the tow fibers are bonded at least at some part of their length. The tow fibers 9 are except at the bonding sites unbonded to each other.

The bonding pattern can be the same over the entire acquisition layer 5 or be different in different parts thereof, thus the bonding pattern can be more sparse in the wetting area and tighter outside thereof. It is also possible to design the bonding pattern in such a way that the layer 5 will have different thickness in different parts of the article, for example thinner in the central portions thereof and thicker in the surrounding edge portions in order to create a bowl shape which provides a liquid receiving volume, alternatively thicker in the central portions than in the surrounding edge portions in order to provide a better body contact.

The layer 15 of tow fibers 9 according to the invention can, besides as a liquid acquisition layer in an absorbent article, be arranged as a topsheet material closest to the wearer or as a combined topsheet/acquisition layer. It can also be bonded to a carrier material, for example a nonwoven.

Figure 4:
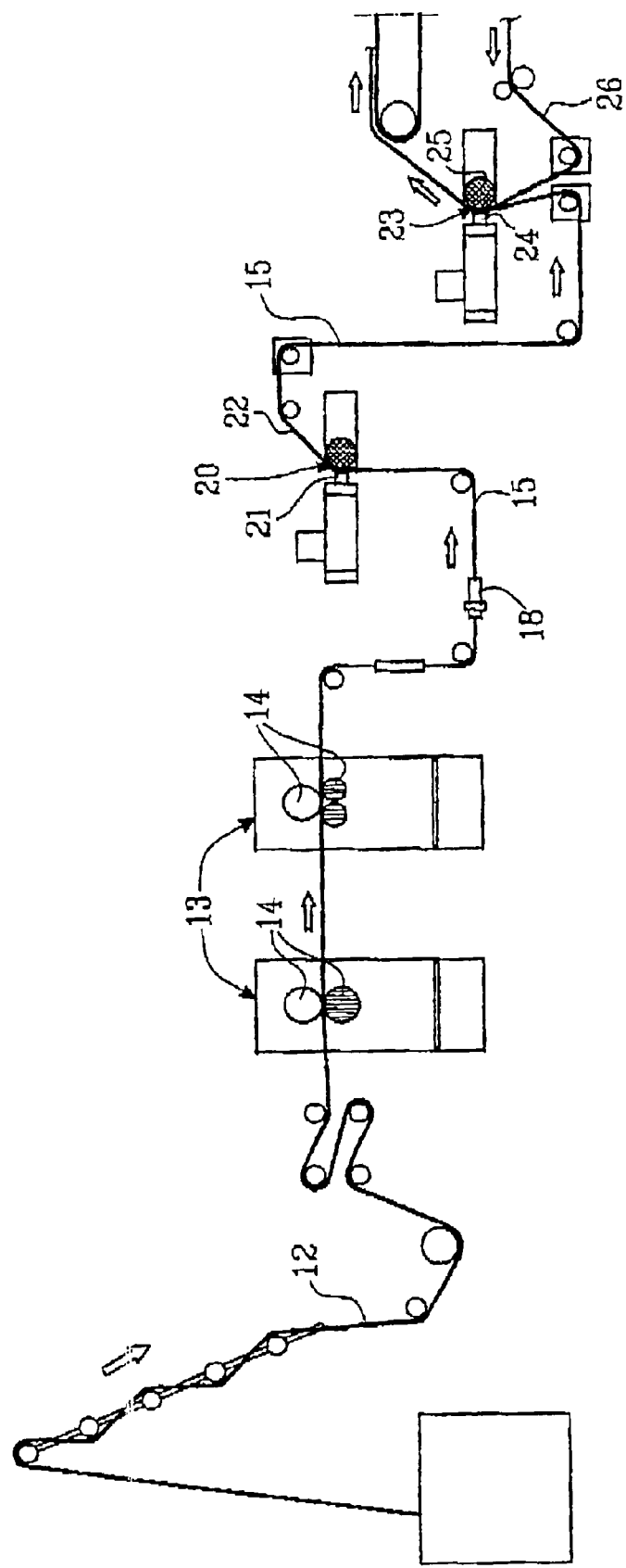
FIG. 4 is a schematic side view of a process equipment for performing the method according to the invention.

The method of producing the material layer according to the invention comprises several steps, which are schematically illustrated in FIG. 4. Fiber tow 12 is supplied in sacks or in the form of bales or rolls of continuous tow fibers, which either are straight, crimped or curled. Crimped or curled fibers are preferred in this case since they provide a very open and airy structure. The fibers in the tow can be of any suitable material such as polyethylene, polypropylene, polyamide, polyester, polylactide, polyvinyl acetate, cellulose acetate, regenerated cellulose such as viscose and rayon, or of bicomponent type with a shell of a polymer having a lower melting point and a core of a polymer having a higher melting point. Specially preferred are such fibers having a high resiliency, for example polyester, copolyester and polypropylene.

The fiber thickness can vary but should be in the interval 0.5 to 10 dtex, preferably 1.5 to 25 and most preferably 2–15 dtex, if the material is to be used as an acquisition layer. The open airy structure in combination with the relatively coarse fiber dimension gives a very rapid liquid acquisition. Besides the material is strong due to the continuous fibers which provide strength in the longitudinal direction, and the bonding pattern which provides strength in the transverse direction.

The bales or the like are opened in special opening equipments in which the tow fibers are separated from each other, stretched and spread out to an essentially evenly thick layer of tow fibers. The tow layer is bonded in the desired bonding pattern according to above and is cut in suitable lengths either before or after application in an absorbent article. The bonding can alternatively be made after cutting. A tow is a relatively cheap delivery form of fibers as compared to nonwoven, waddings or the like which are normally used as acquisition materials.

As can be seen from FIG. 4 the opening device 13 comprises one or more pairs of rolls forming a roll nip, said rolls either being smooth or one roll is threaded and the opposite roll is a counter roll, the fiber tow being fed through said roll nip(s), which provides a separation of the fibers. The tow fibers are stretched during their passage through the roll nip(s) 14. This type of opening devices are of conventional kind and are available on the market in different constructions.

According to the embodiment shown in FIG. 4 the opened fiber tow, which now is in the form of a spread-out layer of separated individual tow fibers 9, is led through an ejector 18 which blows air into the material web 15 substantially in the longitudinal direction thereof. This ejector and through-air blowing is optional, depending on the quality of the fiber tow, and is used for increasing volume and bulkiness of the material web. The device may comprise further means for controlling the fiber distribution in the transverse direction before entering the bonding station 20, such as folding means for longitudinally folding the tow layer one or more times and/or guiding means having a certain cross sectional shape through which the tow layer 15 is fed. A more detailed description of a method and device for making a bonded tow layer is found in EP-A-937 792, the content of which is incorporated herein by reference.

The tow layer 15 is then fed to a first bonding station 20, which in this embodiment is an ultra sonic welding device. This comprises an ultra sonic horn 21 arranged just opposite a pattern roll 22.

The pattern roll 22 can besides a macropattern, e.g. a pattern of lines or other optional pattern, be provided with a micropattern, in the form of an uneven or grooved surface, on the top surface of the protruded parts of the pattern roll 22. By the micropattern the total welding surface is divided in smaller parts, at which there will be less material to melt and the friction between the material web and the ultrasonic welding device is reduced. The height of the micropattern is of the magnitude tenth parts of a millimeter, this applies also for their length and width. The micropattern makes it possible to weld at higher speeds without risk that the joint breaks during bonding. It would also be possible to weld an uneven material web, i.e. in which the material thickness varies across the machine direction.

It would also be possible to have an uneven or grooved surface on the ultrasonic horn 21.

In the first bonding station 20 a relatively strong and diffuse first bonding pattern 10a is created. This is achieved by the fact that the pattern roll 22 is driven at a somewhat higher speed than the feeding speed of the tow layer 15. The speed of the pattern roll 22 should be at least 8%, preferably between 8 and 100% and more preferably between 10 and 25% higher than the feeding speed of the tow layer 15. The speed difference leads to that the welding points gets diffuse but relatively stronger than bonding points created by driving the pattern roll 22 at the same speed as the feeding speed of the tow layer 15.

As is mentioned above other types of thermal bonding methods than ultrasonic welding can be used, such as pattern calendering, laser bonding etc. The second bonding pattern may also be provided by other bonding techniques than thermal bonding, such as by gluing or mechanical bonding.

The tow layer 15 is after the first bonding station 20 fed to a second bonding station 23, which in this embodiment also is an ultra sonic welding device. This comprises an ultra-sonic horn 24 arranged just opposite a pattern roll 25. In this second bonding station 23 the pattern roll 25 is driven at substantially the same speed as the feeding speed of the tow layer 15. The bonding pattern 10b formed in the tow layer 15 will then be relatively distinct. Since it is applied on top of the first bonding pattern 10a it will be the most visible of the two bonding patterns.

The first and second bonding patterns are applied so as to be overlapping over at least a substantial part, meaning at least 50%, of the bonded area of the tow layer. The term overlapping does not necessarily mean that the individual bonding sites have to overlap or cross each other, but that the bonding patterns are overlapping.

There are several advantages achieved by the present invention. Firstly the strength in transverse direction of the bonded tow layer is considerably increased by the first relatively diffuse bonding pattern. An increase of at least 50% of the transverse strength has been achieved as compared to the strength obtained by a distinct bonding pattern provided by driving the pattern roll with the same speed as the tow layer. A further advantage is that the tow layer is evened in the first bonding station, so that it when entering the second bonding station is more even than it would have been otherwise. The second bonding is therefore improved with a reduced risk for loose fibers sticking out.

In the embodiments shown in the drawings the first and second bonding patterns 10a and 10b are different with the second bonding pattern 10b being more dense than the first more diffuse bonding pattern 10a. It is of course possible to have a more dense first bonding pattern and also to have the same first and second bonding patterns Bonding density or tightness, is defined as the number of bonding sites per area unit.

The bonding pattern comprises a plurality of bonding sites in the form of points, lines, spots or the like arranged in a pattern. The bonding area of a bonding pattern is defined as the amount of the pattern that consists of the bonding sites. The first and second bonding patterns may have substantially the same or different bonding areas.

It is pointed out that by relatively large bonding sites, for example in the form of lines, a relatively large bonding area may be provided with a relatively small number of bonding sites, as compared to a bonding pattern of small bonding sites, for example in the form of points, which have to arranged tighter in order to provide the same bonding area as for a pattern of larger bonding size. Thus both bonding area and bonding tightness are important.

The bonding sites, when these have a length extension in one main direction, such as lines, of the first and second bonding patterns may further have the same or different angles with respect to the main direction of the tow fibers 9, so that for example the bonding lines or the like of the first bonding pattern are arranged more close to a perpendicular direction with respect to the main direction of the tow fibers as compared to the bonding lines of the second bonding pattern or vice versa. By this an increase of the bonding strength in the transverse direction of the layer is achieved. The bonding lines within the first and second bonding patterns may also have different angles with respect to the main direction of the tow fibers.

In this second bonding station 23 the tow layer can possibly be laminated to a nonwoven material 26 or a plastic film, which may be perforated or breathable. The nonwoven material 26 or the like can either be laminated to the tow layer 15 over the entire width thereof or in the form of strips be laminated only to the edges of the material web. The nonwoven material 26 or the like, which is either hydrophobic or hydrophilic, serves to prevent spreading of liquid toward the edges of the absorbent article and to prevent rewetting of liquid towards the skin of the wearer.

The pattern bonded tow layer 15, which optionally has been laminated to a nonwoven material or the like, can then either be wound on a winding roll or directly fed into a diaper machine or the like, where it is applied as a layer in an absorbent article such as a diaper, a pant diaper, an incontinence guard, a sanitary napkin or the like.

What is claimed is:

1. A method of producing a fibrous material layer mainly intended for being incorporated in an absorbent article, selected from the group consisting of a diaper, pant diaper, incontinence guard, sanitary napkin, and wound dressing, which comprises:
    opening at least one bundle of continuous fibers, so called tow;
    separating the tow fibers and evening the tow to a layer having the desired fiber distribution; and
    bonding the tow layer in a bonding pattern, but where the tow fibers otherwise are substantially unbonded to each other, wherein bonding is performed in two steps:
    a first step wherein bonding takes place by thermobonding, at which a pattern roll is used which provides the desired bonding pattern, said pattern roll being driven at a higher speed than the feeding speed of the tow layer, so as to create a relatively diffuse and strong bonding pattern in the tow layer; and
    a second step in which a more distinct second bonding pattern is created.

2. A method as claimed in claim 1, wherein said first and second bonding patterns are applied so as to overlap with each other over at least a substantial part of the bonded area of said fibrous material layer.

3. A method as claimed in claim 1, wherein in the second step bonding also takes place by thermobonding, at which a pattern roll is used which provides the desired bonding pattern.

4. A method as claimed in claim 3, wherein in the second bonding step the pattern roll is driven at substantially the same speed as the feeding speed of the tow layer.

5. A method as claimed in claim 3, wherein the speed of the pattern roll of the first bonding step is at least 8% higher than the feeding speed of the tow layer.

6. A method as claimed in claim 5, wherein the speed of the pattern roll of the first bonding step is between 8 and 100% higher than the feeding speed of the tow layer.

7. A method as claimed in claim 6, wherein the speed of the pattern roll of the first bonding step is between 10 and 25% higher than the feeding speed of the tow layer.

8. A method as claimed in claim 1, wherein in the second step the tow layer is laminated to a web of material.

9. A fibrous material layer produced by the method of claim 1.

10. A fibrous material layer mainly intended for being incorporated in an absorbent article, selected from the group consisting of a diaper, pant diaper, incontinence guard, sanitary napkin, and wound dressing, said material layer comprising a layer of continuous fibres, so-called tow, which have been bonded together in points, lines or spots in a bonding pattern, but otherwise are substantially unbonded to each other, wherein the tow layer is bonded with at least two bonding patterns:
    a first relatively strong and diffuse bonding pattern provided by thermobonding, and
    a second more distinct bonding pattern;
    said first and second bonding patterns being arranged so as to overlap with each other over at least a substantial part of the bonded area of said fibrous layer.

11. A fibrous material layer as claimed in claim 10, wherein the second bonding pattern is also a thermobonded bonding pattern.

12. A fibrous material layer as claimed in claim 10, wherein a web of material is laminated to the tow layer with said second bonding pattern.

13. A fibrous layer as claimed in claim 10, wherein at least a part of the continuous fibres in said tow layer are crimped or curled.

14. A fibrous layer as claimed in claim 10, wherein the first and second bonding patterns comprise dots, spots or lines which cross the longitudinal direction of the tow fibers.

15. A fibrous layer as claimed in claim 14, wherein individual bonding sites of the first and second bonding patterns have a length extension in one main direction, and the bonding lines of the first bonding pattern are arranged at a different angle to the main direction of the tow fibers as compared to the bonding lines of the second bonding pattern.

16. A fibrous layer as claimed in claim 14, wherein individual bonding sites of the first and second bonding patterns have a length extension in one main direction, and the bonding lines within the first and/or the second bonding pattern have different angles with respect to the main direction of the fibers.

17. A fibrous layer as claimed in claim 14, wherein different bonding sites overlap each other, as seen in the transverse direction of the article, so that a main portion of the tow fibers are bonded at least at some part of their length.

18. An absorbent article selected from the group consisting of a diaper, pant diaper, incontinence guard, sanitary napkin, and wound dressing, comprising a liquid permeable topsheet, a liquid impervious backsheet and an absorbent body arranged therebetween, wherein the article comprises a tow layer as claimed in claim 10.

19. An absorbent article according to claim 18, wherein the tow layer is used as a liquid acquisition layer applied between the topsheet and the absorbent body.

20. An absorbent article according to claim 18, wherein the tow layer is used as a liquid pervious topsheet.

21. An absorbent article according to claim 18, wherein the tow layer is used as an integrated topsheet/liquid acquisition layer.

* * * * *